(12) United States Patent
Sands

(10) Patent No.: US 6,255,334 B1
(45) Date of Patent: Jul. 3, 2001

(54) 5HT$_1$ RECEPTOR AGONISTS AND METOCLOPRAMIDE FOR THE TREATMENT OF MIGRAINE

(75) Inventor: George H. Sands, New York, NY (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/387,990

(22) Filed: Sep. 1, 1999

Related U.S. Application Data

(60) Provisional application No. 60/106,328, filed on Oct. 30, 1998.

(51) Int. Cl.$^7$ .......................... A61K 31/40; A61K 31/16
(52) U.S. Cl. .......................... 514/414; 514/626; 514/323; 514/383; 514/415
(58) Field of Search .......................... 514/323, 383, 514/414, 415, 626

(56) References Cited

U.S. PATENT DOCUMENTS 5,698,571 * 12/1997 Audia et al. ..................... 514/423

FOREIGN PATENT DOCUMENTS 2325161 11/1998 (GB).
98/02186 * 1/1998 (WO).

OTHER PUBLICATIONS

Kelly A M et al.: "Intravenous chlorpromazine versus intramuscular sumatriptan for acute migraine." *Journal of Accident and Emergency Medicine*, (Jul. 1997) 14 (4) 209—11., XP000869766–page 210, col. 1, line 31–line 52.

Von Seggern R L et al.: "Cost consideration in headache treatment. Part 2: Acute migraine treatment."*Headache*, (Sep. 1996) 36 (8) 493–502., XP000869685—p. 494, col. 1, line 26—line 48; page 498, column 1, line 7 line 13; page 501, column 1, line 1–line 12.

Schwarzberg M N: "Application of metoclopramide specificity in migraine attacks therapy."*Headache*, (Jul.–Aug. 1994) 34 (7) 439–41., XP000869686—p. 440, col. 1, line 1–line 11; p. 440, column 2, line 49—p. 441, col. 1, line 3.

Seaber E J et al: "The novel anti–migraine compound zolmitriptan (Zomig 311C90) ha no clinically significant interactions with paracetamol or metoclopramide." *European Journal of Clinical Pharmacology*, (1997) 53 (3–4) 229–34, XP000870485 abstract, p. 229, col 2, paragraph 2, table 1.

Rolan, P.: "Potential drug interations with the novel antimigraine compound zolmitriptan (Zomig, 311C90)." *Cephalalgia*, (Oct. 1997.) 17 Suppl 18 21—7. Ref. XP000870490, abstract p. 23, col. 2, paragraph 1.

* cited by examiner

*Primary Examiner*—Rebecca Cook
(74) *Attorney, Agent, or Firm*—Peter C. Richardson; Paul H. Ginsburg; Israel Nissenbaum

(57) ABSTRACT

The present invention relates to a method of treating migraine in a mammal, including a human, by administering to the mammal a 5HT$_1$ receptor agonist, and particularly eletriptan, in combination with metoclopramide. It also relates to pharmaceutical compositions containing a pharmaceutically acceptable carrier, a 5HT$_1$ receptor agonist and metoclopramide.

5 Claims, No Drawings

5HT₁ RECEPTOR AGONISTS AND METOCLOPRAMIDE FOR THE TREATMENT OF MIGRAINE

This application claims priority to U.S. Provisional application No. 60/106,328 field Nov. 30, 1998.

The present invention relates to a method of treating migraine in a mammal, including a human, by administering to the mammal a 5HT₁ receptor agonist in combination with metoclopramide. It also relates to pharmaceutical compositions containing a pharmaceutically acceptable carrier, a 5HT₁ receptor agonist and metoclopromide. Examples of agonists of 5HT₁ receptors are agonists of one or more of the 5HT$_{1A}$, 5HT$_{1B}$, 5HT$_{1C}$, 5HT$_{1D}$, 5HT$_{1E}$, and 5HT$_{1F}$ receptors.

The combined use of metoclopramide and 5HT₁ agonists (e.g. eletriptan, rizatriptan, naratriptan, sumatriptan, but excluding zolmitriptan) for the acute treatment of migraine offers enhanced efficacy and less nausea than currenty used therapies.

In 1975, Volans showed that metoclopramide helped alleviate the gastric stasis that accompanies migraine attacks. (See Volans, G. N., *British Journal of Pharmacology*, 1975 February; 2(1): 67–73; and Volans, G. N., *Clinical Pharmacokinetics*, 1978 July; 3(4): 313–318.) He studied this effect and showed the blood levels of aspirin and acetaminophen (paracetamol), taken orally, were decreased in patients experiencing a migraine attack, and that these levels returned to normal in between migraine attacks. The use of metoclopramide with aspirin or acetaminophen increased the blood levels of these medications, making them more efficatious for the treatment of migraine.

It is believed that 5HT₁ agonists would exhibit substantially greater efficacy for the treatment of migraine when administered in combination with metoclopramide, in view of the increased blood levels of the oral 5HT₁ agonist and the antiemetic and antimigraine action of metaclopramide.

Metoclopramide is a benzamide derivative, and, although it is related to the neuroleptics, it has no significant antipsychotic or sedative properties. Metoclopramide is a dopamine and 5HT₃ receptor antagonist and also possesses some 5HT₄ agonist activity. The actions of metoclopramide include antagonism of emesis induced by apomorphine or ergotamine. It also induces hyperprolactinemia, a characteristic of dopaminergic blockade. Metoclopramide has relatively low affinity for the dopamine-2 (D2) receptor.

SUMMARY OF THE INVENTION

The present invention relates to pharmaceutical compositions for the treatment of migraine in a mammal, including a human, comprising metoclopramide; a 5HT₁ receptor agonist, or a pharmaceutically acceptable salt thereof, excluding zolmitriptan; and a pharmaceutically acceptable carrier.

This invention also relates to a method of treating migraine in a mammal, including a human, comprising administering to said mammal an amount of a pharmaceutical composition comprising metoclopramide; a 5HT₁ receptor agonist, or a pharmaceutically acceptable salt thereof, excluding zolmitriptan; and a pharmaceutically acceptable carrier; that is effective in treating migraine.

This invention also relates to a method of treating migraine in a mammal, including a human, comprising administering to said mammal metoclopramide; a 5HT₁ receptor agonist, or a pharmaceutically acceptable salt thereof, excluding zolmitriptan; in amounts that render the combination of such two active agents effective in the treatment or prevention of migraine.

Preferred embodiments of this invention relate to pharmaceutical compositions for the treatment of migraine and methods of treating migraine, as described above, wherein the 5HT₁ receptor agonist is selected from eletriptan, naratriptan, rizatriptan, sumatriptan almotriptan, avitriptan, frovatriptan, alniditan, LY 334370, LY 306258, BMS-180048 and BMS-181885. A most highly preferred embodiment is the pharmaceutical combination of eletriptan and metoclopramide wherein it is also expected that the pharmacokintetics of the eletriptan would be enhanced.

Other embodiments of this invention relate to pharmaceutical compositions for the treatment of migraine and methods of treating migraine, as described above, wherein the 5HT₁ receptor agonist is a compound of the formula

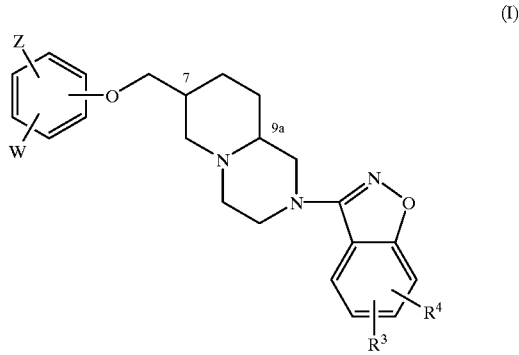

(I)

wherein $R^3$, $R^4$, and Z are selected, independently, from hydrogen, halo (e.g., chloro, fluoro, bromo or iodo), ($C_1$–$C_4$) alkyl optionally substituted with from one to three fluorine atoms, ($C_1$–$C_4$)alkoxy optionally substituted with from one to three fluorine atoms, and ($C_1$–$C_4$)alkoxy-($C_1$–$C_4$)alkyl wherein each of the alkyl moieties may optionally be substituted with from one to three fluorine atoms;

W is —CH₂—O—($C_1$–$C_6$) alkyl wherein the alkyl moiety can be straight or branched;

or W is —CH₂NR¹R² wherein $R^1$ and $R^2$ are independently selected from hydrogen and straight or branched ($C_1$–$C_6$)alkyl;

or $R^1$ and $R^2$, together with the nitrogen to which they are attached, form a saturated four membered monocyclic ring or a saturated or unsaturated nonaromatic five to seven membered monocyclic ring or a saturated or unsaturated nonaromatic seven to ten membered bicyclic ring which may optionally contain one or two heteroatoms in addition to the nitrogen of NR¹R², wherein said heteroatoms are independently selected from oxygen, nitrogen and sulfur, and wherein from one to three of the ring carbon atoms, or one of the ring nitrogen atoms, may optionally and independently be substituted with straight or branched ($C_1$–$C_4$) alkyl, straight or branched ($C_1$–$C_6$) alkoxy, straight or branched ($C_1$–$C_3$) alkyl-($C_3$–$C_7$cycloalkyl, hydroxy, amino, cyano, halo, aryl-(straight or branched ($C_1$–$C_3$) alkyl) or heteroaryl-(straight or branched ($C_1$–$C_3$) alkyl), wherein said aryl is selected from phenyl and naphthyl and said heteroaryl is selected from oxazolyl, isoxazoyl, thiazolyl, isothiazolyl, furanyl, pyrazolyl, pyrrolyl, tetrazolyl, triazolyl, thienyl, imidazolyl, pyrazinyl, pyrazolyl, indolyl, isoindolyl, pyrazinyl, cinnolinyl, pyridinyl and pyrimidinyl;

with the proviso that in any ring formed by NR¹R²: (a) there can be no more than one ring oxygen atom; (b) there can be no hydroxy, alkoxy, alkoxyalkyl, cyano, amino or alkylamino moiety bonded directly to any ring nitrogen atom; and (c) no ring carbon that is double bonded to another ring carbon and not part of an aromatic ring system can be bonded to a ring oxygen atom or ring nitrogen atom;

or a pharmaceutically acceptable salt thereof.

DETAILED DESCRIPTION OF THE INVENTION

The following patents and patent applications exemplify $5HT_1$ agonists that can be used, in combination with metoclopramide, in the pharmaceutical compositions and methods of this invention, and refer to methods of preparing the same: U.S. Pat. No. 5,545,644, issued Aug. 13, 1996; European Patent 776,323, granted Feb. 11, 1998; U.S. Pat. No. 5,618,834, issued Apr. 8, 1997; World Patent Application PCT/EP98/04176, which designates the United States and was filed on Jul. 1, 1998; European Patent 503,440, granted Jun. 18, 1998; U.S. Pat. No. 4,816,470, issued Mar. 28, 1989; Japanese Patent 9,423,197, granted Mar. 30, 1994; Canadian Patent 1,241,004, granted Aug. 23, 1988; European Patent 497,512, granted Sep. 24, 1997; U.S. Pat. No. 5,300,506, issued Apr. 15, 1994; European Patent Application 711,769, published May 15, 1996; World Patent Application WO 94/2460, published Feb. 3, 1994; U.S. Pat. No. 5,541,180, issued Jul. 30, 1996; European Patent Application 591,280, published Apr. 13, 1994; European Patent 639,192, granted May 15, 1996; European Patent Application 674,621, published Oct. 4, 1995 and European Patent 486,666, granted Aug. 13, 1997. The foregoing patents and patent applications are incorporated herein by reference in their entireties.

The following references relate to the pharmacological properties of certain of the $5HT_1$ agonists mentioned above as being employed in preferred embodiments of this invention: Robert et al., *Cephalagia* 18(6): 406, July/August 1998; Marathe et al., *Biopharm. Drug Dispos.* 19(6): 381–94, September 1998; Saxena et al., *Eur. J. Pharmacol.* 351(3): 329–39, Jun. 26, 1998; Goldstein et al., *Cephalagia* 18(6): 410, July/August 1998; Buchan et al., *Cephalagia* 18(6): 410, July/August 1998; Block et al., *Cephalagia* 18(6): 409–10, July/August 1998; a Sheftell et al., *Cephalagia* 18(6): 403–4, July/August 1998; Perry et al., *Drugs* (New Zealand) 55(6):889–922, June 1998; Bomhof et al., *Cephalagia* (Norway) 18(1): 33–7, January 1998; Klasson et al., *Headaches* (United States) 37(10): 640–5, November/ December 1997; Goldstein et al., *Cephalagia* (Norway) 16(7): 497–502, November 1996; Parsons et al., *J. Cardiovasc. Pharmacol.* (United States) 32(2): 220–4, August 1998; and Schoenen J., *Curr. Opin. Neurol.* 10(3): 237–43, June 1997. These references are incorporated herein by reference in their entireties.

The term "treating", as used herein, refers to retarding or reversing the progress of, or alleviating or preventing either the disorder or condition to which the term "treating" applies, or one or more symptoms of such disorder or condition. The term "treatment", as used herein, refers to the act of treating a disorder or condition, as the term "treating" is defined above.

This invention relates both to methods of treating migraine in which metoclopramide and the $5HT_1$ receptor agonist are administered together, as part of the same pharmaceutical composition, as well as to methods in which these two active agents are administered separately, as part of an appropriate dose regimen designed to obtain the benefits of the combination therapy. The appropriate dose regimen, the amount of each dose administered, and the intervals between doses of the active agents will depend upon the $5HT_1$ agonist being used, the type of pharmaceutical formulations being used, the characteristics of the subject being treated and the severity of the migraine. Generally, in carrying out the methods of this invention, the $5HT_1$ receptor agonist will be administered orally to an average 70 kg adult human in an amount ranging from about 1 to about 400 mg per day, in single or divided doses, and metoclopramide will be administered in an amount ranging from about 5 to about 125 mg per day, in single or divided doses. Metoclopramide will generally be administered in amounts ranging from about 20 to about 80 mg per day, depending on the severity of the headache and the route of administration. Metoclopramide can be administered orally, intranasally, intravenously, as a rectal suppository or using a "flash" formulation (i.e., allowing the medication to dissolve in the mouth without the need to use water.)

The following table exemplifies preferred dosage ranges of certain specific $5HT_1$ gonists and metoclopramide, when used in combination with each other.

| $5HT_1$ AGONIST | DOSAGE RANGE FOR MEDICATION TAKEN | METOCLOPRAMIIDE DOSAGE RANGE |
| --- | --- | --- |
| Eletriptan | 20 to 80 mg | 5 to 20 mg |
| Rizatriptan | 5 to 10 mg | 5 to 20 mg |
| Sumatriptan | 25 to 100 mg | 5 to 20 mg |
| Naratriptan | 1 to 5 mg | 5 to 20 mg |

The $5HT_1$ receptor agonists that are employed in the pharmaceutical compositions and methods of this invention, and their pharmaceutically acceptable salts, may be administered alone or in combination with pharmaceutically acceptable carriers or diluents. They may be formulated in a conventional manner using one or more pharmaceutically acceptable carriers. Such compounds may be adminstered orally, buccally, intranasally, parenterally (e.g., intravenously, intramuscularly or subcutaneously) or rectally, or in a form suitable for administration by inhalation or insufflation.

For oral administration, the pharmaceutical compositions may take the form of, for example, tablets or capsules prepared by conventional means with pharmaceutically acceptable excipients such as binding agents e.g., pregelatinised maize starch, polyvinylpyrrolidone or hydroxypropyl methylcellulose); fillers (e.g., lactose, microcrystalline cellulose or calcium phosphate), lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in a conventional manner.

The 5HT$_1$ agonists of the invention and their salts may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing andlor dispersing agents.

Alternatively, the active ingredient may be in powder form for reconstitution with a suitable vehicle, e.g., sterile pyrogen-free water, prior to use.

The 5HT$_1$ agonists of this invention and their salts may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Aerosol formulations for the treatment of migraine in the average adult human are preferably made so that each metered dose or "puff" of aerosol contains 20 $\mu$g to 1000 $\mu$g of the compound of the invention. The overall daily dose with an aerosol will generally be within the range of about 100 $\mu$g to 10 $\mu$g. Administration may be several times daily, for example, 2, 3, 4 or 8 times, giving, for example, 1, 2 or 3 doses each time.

The 5-HT$_1$ receptor agonist activity of a compound or salt can be measured in in vitro receptor binding assays as described for the 5-HT$_{1A}$ receptor, using rat cortex as the receptor source and [$^3$H]8-OH-DPAT as the radioligand (D. Hoyer et al., *Europ. J. Pharmacol.*, 1985; 118: 13), and as described for the 5-HT$_D$ receptor, using bovine caudate as the receptor source and [$^3$H]5-HT as the radioligand (R. E. Heuring and S. J. Peroutka, *J. Neuroscience*, 1987; 7: 894).

The in vitro activity of a compound at the 5-HT$_{1D}$ binding site may be determined according to the following procedure. Bovine caudate tissue is homogenized and suspended in 20 volumes of a buffer containing 50 mM TRIS.hydrochloride (tris[hydroxymethyl] aminomethane hydrochloride) at a pH of 7.7. The homogenate is then centrifuged at 45,000G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000G for 10 minutes and the supernatant discarded. The resulting pellet (approximately 1 gram) is resuspended in 150 ml of a buffer of 15 mM TRIS.hydrochloride containing 0.01 percent ascorbic acid with a final pH of 7.7 and also containing 10 mM pargyline and 4 mM calcium chloride (CaCl$_2$). The suspension is kept on ice at least 30 minutes prior to use.

The inhibitor, control or vehicle is then incubated according to the following procedure. To 50 ml of a 20 percent dimethylsulfoxide (DMSO)/80 percent distilled water solution is added 200 ml of tritiated 5-hydroxytryptamine (2 nM) in a buffer of 50 mM TRIS.hydrochloride containing 0.01 percent ascorbic acid at pH 7.7 and also containing 10 mM pargyline and 4 mM calcium chloride, plus 100 nM of 8-hydroxy-DPAT (dipropylaminotetraline) and 100 nM of mesulergine. To this mixture is added 750 ml of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters). The pellet is then washed three times with 4 ml of a buffer of 50 mM TRIS.hydrochloride at pH 7.7. The pellet is then placed in a scintillation vial with 5 ml of scintillation fluid (aquasol 2) and allowed to sit overnight. The percent inhibition can be calculated for each dose of the compound. An IC$_{50}$ value can then be calculated from the percent inhibition values.

The ability of a compound or salt to bind to 5-HT$_{1A}$ receptors can be determined according to the following procedure. Rat brain cortex tissue is homogenized and divided into samples of 1 gram lots and diluted with 10 volumes of 0.32 M sucrose solution. The suspension is then centrifuged at 900G for 10 minutes and the supernatant separated and recentrifuged at 70,000G for 15 minutes. The supernate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at $-70°$ C. until ready for an experiment. The tissue can be thawed immediately prior to use, diluted with 10 mm pargyline and kept on ice.

The tissue is then incubated according to the following procedure. Fifty microliters of control, inhibitor, or vehicle (1 percent DMSO final concentration) is prepared at various dosages. To this solution is added 200 ml of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 ml of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. IC$_{50}$ values are calculated from the percent inhibition values.

The agonist and antagonist activities compounds at 5-HT$_{1A}$ and 5-HT$_{1D}$ receptors can be determined using a single saturating concentration according to the following procedure. Male Hartley guinea pigs are decapitated and 5-HT$_{1A}$ receptors are dissected out of the hippocampus, while 5-HT$_{1D}$ receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra)

of protein per tube. The following agents are added so that the reaction mix in each tube contained 2.0 mM $MgCl_2$, 0.5 mM ATP, 1.0 mM CAMP, 0.5 mM IBMX, 10 mM phosphocreatine, 0.31 mg/mL creatine phosphokinase, 100 mM GTP and 0.5–1 microcuries of [32P]-ATP (30 Ci/mmol: NEG-003—New England Nuclear). Incubation is initiated by the addition of tissue to siliconized microfuge tubes (in triplicate) at 30° C. for 15 minutes. Each tube receives 20 mL tissue, 10 mL drug or buffer (at 10×final concentration), 10 mL 32 nM agonist or buffer (at 10×final concentration), 20 mL forskolin (3 mM final concentration) and 40 mL of the preceding reaction mix. Incubation is terminated by the addition of 100 mL 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 mM (R)-8-OH-DPAT for 5-$HT_{1A}$ receptors, and 320 nM 5-HT for 5-$HT_{1D}$ receptors. Percent inhibitions by the test compounds are then calculated in relation to the inhibitory effect of (R)-8-OH-DPAT for 5-$HT_{1A}$ receptors or 5-HT for 5-$HT_{1D}$ receptors. The reversal of agonist induced inhibition of forskolin-stimulated adenylate cyclase activity is calculated in relation to the 32 nM agonist effect Compounds can be tested for in vivo activity for antagonism of 5-$HT_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a 5-$HT_{1D}$ agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-$HT_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and 5-$HT_{1D}$ agonists are given concurrently and temperatures are taken at 30, 60, 120 and 240 minutes later.

Data are analyzed with two-way analysis of variants with repeated measures in Newman-Keuls post hoc analysis.

The 5-$HT_1$ agonist activity can be determined by the in vitro receptor binding assays, as described for the 5-$HT_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-$HT_{1D}$ receptor using bovine caudate as the receptor source and [3H] serotonin as the radioligand [R. E. Heuring and S. J. Peroutka, *J. Neuroscience*, 7, 894 (1987)]. Of the active compounds tested, all exhibited an $IC_{50}$ in either assay of 1 mM or less.

Compounds and salts can be evaluated as anti-migraine agents by testing the extent to which they mimic sumatriptan in contracting the dog isolated saphenous vein strip (P. P. A. Humphrey et al., *Br. J. Pharmacol.*, 1988; 94:1128.). This effect can be blocked by methiothepin, a known serotonin antagonist. Sumatriptan is known to be useful in the treatment of migraine and produces a selective increase in carotid vascular resistance in the anaesthetized dog. It has been suggested that this is the basis of its efficacy by Fenwick et al., *British Journal of Pharmacology.*, 1989; 96: 83.

What is claimed is:

1. A pharmaceutical composition for the treatment of migraine comprising eletriptan, metoclopramide and a pharmaceutically acceptable carrier.

2. A method of treating migraine in a mammal, comprising administering to said mammal, metoclopramide and eletriptan, in amounts that render the combination of said two active agents effective in the treatment of migraine.

3. A method according to claim 2, wherein the eletriptan and metoclopramide are administered separately according to a dose regimen that renders the combination of the separately administered active agents effective in the treatment of migraine.

4. A method according to claim 2, wherein the eletriptan is administered in an amount from about 1 mg to about 400 mg per day and metoclopramide is administered in an amount from about 5 mg to about 125 mg day.

5. A method for enhancing the pharmacokinetics of eletriptan for treatment of migraine in a mammal, comprising utilizing elitriptan with metoclopramide.

* * * * *